US011484476B2

(12) United States Patent
Savoldi et al.

(10) Patent No.: US 11,484,476 B2
(45) Date of Patent: Nov. 1, 2022

(54) ELECTRO-CONDUCTIVE AND ANTI-BACTERIAL COMPOSITE MATERIAL, FOR ENDODONTIC USE

(71) Applicant: THE UNIVERSITY OF HONG KONG, Hong Kong (CN)

(72) Inventors: Fabio Savoldi, Brescia (IT); Jukka Pekka Matinlinna, Hong Kong (CN); Kit Hon James Tsoi, Hong Kong (CN); Corrado Paganelli, Brescia (IT); Luca Visconti, Brescia (IT); Giovanni Rasia Dal Polo, Brescia (IT)

(73) Assignee: THE UNIVERSITY OF HONG KONG, Hong Kong (CN)

( * ) Notice: Subject to any disclaimer, the term of this patent is extended or adjusted under 35 U.S.C. 154(b) by 575 days.

(21) Appl. No.: 16/339,961

(22) PCT Filed: Oct. 6, 2016

(86) PCT No.: PCT/CN2016/101434
§ 371 (c)(1),
(2) Date: Apr. 5, 2019

(87) PCT Pub. No.: WO2018/064798
PCT Pub. Date: Apr. 12, 2018

(65) Prior Publication Data
US 2019/0282454 A1 Sep. 19, 2019

(51) Int. Cl.
*A61K 6/52* (2020.01)
*A61K 33/38* (2006.01)
(Continued)

(52) U.S. Cl.
CPC .............. *A61K 6/52* (2020.01); *A61K 6/54* (2020.01); *A61K 6/842* (2020.01); *A61K 33/38* (2013.01); *A61K 6/56* (2020.01)

(58) Field of Classification Search
CPC ...................................................... A61K 6/52
See application file for complete search history.

(56) References Cited

U.S. PATENT DOCUMENTS

| 3,863,345 A | 2/1975 | Malmin |
| 4,525,147 A | 6/1985 | Pitz et al. |

(Continued)

FOREIGN PATENT DOCUMENTS

| CN | 103976882 A | 8/2014 |
| CN | 104921955 A | 9/2015 |

(Continued)

OTHER PUBLICATIONS

International Search Report and Written Opinion in corresponding PCT Application No. PCT/CN2016/101434, dated Jun. 30, 2017.

(Continued)

*Primary Examiner* — Michael F Pepitone
(74) *Attorney, Agent, or Firm* — Leason Ellis LLP (57) ABSTRACT

A gutta-percha-silver composite with determined weight percentage and particle size, is provided. The composite exhibits electro-conductivity greater than the standard gutta-percha composites. The new material simplifies root canal treatments, shortens the times both for clinician and patients, and reduces the exposure to patients from X-rays. The material is not only electro-conductive; it is anti-bacterial, which improves the outcomes of the procedures. Also, it has improved thermal conductivity, and mechanical properties.

18 Claims, 7 Drawing Sheets

(51) Int. Cl.
   *A61K 6/842* (2020.01)
   *A61K 6/54* (2020.01)
   *A61K 6/56* (2020.01)

(56) References Cited

U.S. PATENT DOCUMENTS

| | | | |
|---|---|---|---|
| 4,526,179 A | 7/1985 | Salesky | |
| 5,263,861 A | 11/1993 | Cohen et al. | |
| 5,588,835 A | 12/1996 | Kert | |
| 6,254,392 B1* | 7/2001 | Mannschedel | A61C 5/50 433/224 |
| 6,270,343 B1 | 8/2001 | Martin | |
| 9,192,545 B2 | 11/2015 | Li | |
| 2006/0185170 A1 | 8/2006 | Lewis et al. | |
| 2007/0262094 A1* | 11/2007 | Muller | A61C 5/62 222/327 |
| 2008/0038697 A1* | 2/2008 | Pavlov | A61C 5/50 433/224 |
| 2010/0124728 A1 | 5/2010 | Walia | |
| 2011/0256383 A1* | 10/2011 | Cochet | C08K 3/10 428/328 |
| 2013/0056908 A1 | 3/2013 | Goodis et al. | |

FOREIGN PATENT DOCUMENTS

| | | |
|---|---|---|
| EP | 0951875 A2 | 10/1999 |
| EP | 1219261 A2 | 7/2002 |
| GB | 381774 A | 10/1932 |
| JP | 3611843 B1 | 1/2005 |
| WO | WO-2008/102214 A2 | 8/2008 |
| WO | WO-2007/126751 A2 | 11/2008 |
| WO | WO-2013/181105 A1 | 12/2013 |
| WO | WO-2013/190539 A1 | 12/2013 |

OTHER PUBLICATIONS

Nishikawa H., et al., "Root canal filling with electrically conductive gutta-percha point", *Josai Shika Daigaku Kiyo*, 1981;10(3), pp. 393-402.

Rivera E. M., et al., "Placement accuracy of electrically conductive gutta-percha", *Journal of Endodontics*. Jul. 1994, 20(7), pp. 342-344.

* cited by examiner

ELECTRO-CONDUCTIVE AND ANTI-BACTERIAL COMPOSITE MATERIAL, FOR ENDODONTIC USE

CROSS-REFERENCE TO RELATED APPLICATIONS

This application is a U.S. National Phase Application under 35 U.S.C. § 371 of International Patent Application No. PCT/CN2016/101434, filed Oct. 6, 2016, which is incorporated herein by reference in its entirety. The International Application was published on Apr. 12, 2018 as No. WO/2018/064798 A1.

FIELD OF THE INVENTION

The invention is about a root canal filling material to be used in the treatment of endodontic infections. The material consists of a mixture of gutta-percha, a rubber commonly used in root canal treatments, and silver particles. This new material, compared to the standard gutta-percha, has electro-conductive properties, and can be used together with electronic devices to control the accuracy of the position of the root canal filling material during the clinical procedures.

BACKGROUND OF THE INVENTION

The invention is related to the field of dentistry, especially to the field of endodontics. Among the endodontic treatments, the root canal treatment is widely diffused and has demonstrated efficacy for several decades.

The ultimate objective of root canal treatment is to eliminate the infection inside the dental root canal system and in the surrounding tissues, tightly sealing the root canal system with its complex channels and small openings in the root structure, and especially the tiny opening at the end of the root canal (root canal apex). Failure to completely seal the root canal system may lead to micro-leakage and may lead to future bacterial colonization inside the root canal system and the surrounding soft and hard tissues, and possibly re-infection leading even to the loss of the tooth.

In order to properly seal the root canal system, a root canal filling material with special requirements is needed, such as dimensional stability, biocompatibility and radiopacity. It should be easy to remove, not stain the tooth structure, inexpensive and easy to use.

Gutta-percha composites are the commonly used material for this purpose. Gutta-percha is a natural polymer prepared from the latex of a specific tree (the percha tree), and it is usually manufactured and delivered as specific sets of gutta-percha points (or cones) of various sizes.

Root canal treatment is a clinical procedure generally following a sequential protocol usually starting with local anaesthesia, followed by removal of the decayed part of the tooth, then creation of an access point in the tooth to expose the nerve, cleaning out of the infected nerve tissue and shaping of the root canal system accordingly to clinical requirements. While so doing, the root canal system is irrigated with an antibacterial agent, and dried afterwards. Finally, an inert material such as gutta-percha, which is usually point-shaped and either cold or heated-softened, is used to fill the now hollow root canal system of the tooth without voids. See U.S. Pat. Nos. 6,270,343 and 3,863,345, which are incorporated herein by reference in their entirety.

The proper positioning of the gutta-percha point, in order to obtain sealing of the root canal system, is fundamental for the healing of the infection. For this reason, the gutta-percha composite should be used to fill the root canal system up to the root canal apex, and exactly to the root canal apex. In order to do so, it is necessary to know the length of the root canal, and this is usually accomplished either by taking an X-ray with a metallic probe (file) of a known length, or using a dedicated device (apex-locator) connected to a metallic probe (file) of known length. See U.S. Pat. No. 4,526,179, which is incorporated herein by reference in its entirety. The use of an apex-locator is the gold standard in endodontic treatment, and most dentists use it. This device can precisely estimate the root canal length using electrical resistivity principles.

The gutta-percha composite is usually provided in cone-shaped points; these points have to be inserted into the root canal with their tip precisely reaching the root canal apex. Thanks to the previous length measurements, the dentist knows the length of the root canal and can insert the gutta-percha point of the right amount to fill the root canal system exactly to the root canal apex. See U.S. Pat. No. 5,588,835, which is incorporated herein by reference in its entirety.

The prior art has some disadvantages related to the achievement of the proper positioning of the gutta-percha point. Although the length of the root canal is known, since a high precision is required and the gutta-percha point may bend, and because the metallic probe (file) previously used is made of a different material from a gutta-percha point, after inserting the real gutta-percha point at the supposed correct position, an X-ray is necessary to check that the tip of the gutta-percha point is actually at the root canal apex. Gutta-percha composites are made radiopaque with addition of heavy metals to allow this verification.

Furthermore, although the X-ray is used to check the correctness of the position of the gutta-percha point, it has limitation as well (above the effects of ionizing radiation), determined by its two-dimensional nature applied in a three-dimensional root canal system. In fact, the root canal apex may be not at the tip of the root, e.g., it may be on the side of the root. In fact, the root canal is often not in the centre of the root, i.e., it does not follow the main axis of the root, eventually having its opening not at the tip of the root. This generates a difference between the so-called "radiographic apex" (located at the tip of the root), and the so-called "clinical apex" (the root canal apex, located at the end of the root canal). The correct endodontic treatment should aim at sealing the root canal system to the clinical apex, and not the radiographic apex. Unfortunately, if the clinical apex is different from the radiographic apex, although the gutta-percha point is properly positioned reaching the clinical apex, the X-ray may show the gutta-percha point as not properly positioned (i.e., it will appear shorter than the radiographic apex even if matching the root canal apex). Furthermore, when the clinical apex is different from the radiographic apex, if the gutta-percha point is not properly positioned and it protrudes outside the clinical apex, the X-ray may not allow identification of the problem (i.e., the gutta-percha point may appear shorter or properly positioned). This problem can be avoided with the use of an apex-locator.

Currently, only if this X-ray confirms that the tip of the gutta-percha point matches the root canal apex, will the gutta-percha composite then be permanently stabilized. This final procedure can be performed mainly with two techniques: a hot technique (i.e., vertical condensation of warm gutta-percha) in which one or more gutta-percha points are heat-softened and packed with a metallic carrier, to make them permanently adhere to the root canal system walls, or a cold technique (i.e., lateral condensation of cold gutta-percha) which stabilizes one or more gutta-percha points with root canal cement. Finally, the tooth is sealed with a filling material (such as amalgam or composite) and, in some cases, prepared for a crown.

Therefore, the traditional root canal treatment has several limitations, such as the need for numerous X-ray pictures, which leads to exposure of the patient to radiation. Also, it requires extra-time for performing the X-rays, which considerably extends the duration of the medical procedures. Further, it requires increased utilization of supporting materials, such as for the X-ray pictures.

SUMMARY OF THE INVENTION

The use of root canal filling materials for endodontic treatments is a well-established and safe method that has been used for a long time. According to the present invention, new root canal filling materials with electro-conductive and anti-bacterial properties are provided. These materials can be used in the production of endodontic points or other endodontic products and, compared to the previous art, can reduce the need for intra-operative X-rays (because they can be used with electronic devices, e.g. apex-locators) and further help in infection-control after the endodontic procedures.

This new composite material has new and different physical properties from prior materials, especially because it is electro-conductive and can therefore be used with electronic devices. However, it maintains the basic characteristics of adhesion to the root canal system walls as exhibited by the prior art gutta-percha composite (i.e., it has a good sealing effect).

The present invention provides the use of a metallic powder in an endodontic filling material for root canal treatment to form a mixture of gutta-percha-based material and said metallic powder exhibiting enough electro-conductivity that it is detectable with an electronic apex-locator.

The present invention further provides an endodontic filling material for root canal treatment, comprising:
gutta-percha-based material and
a metallic powder mixed with the gutta-percha-based material in sufficient quantity to form a mixture exhibiting enough electro-conductivity that it is detectable with an electronic apex-locator.

In one embodiment of the present invention, the metallic powder is power of silver, titanium, stainless steel, graphite, aluminium, copper, gold or the mixture thereof.

In one embodiment of the present invention, the amount of the metallic powder in the mixture is 1-99% by weight, 5-95% by weight, 10-90% by weight, 40-90% by weight, 50-90% by weight, 50-60% by weight, 60-80% by weight, 60-70% by weight, 30-50% by weight, 30-40% by weight, 20-30% by weight, or greater than 50% by weight.

In one embodiment of the present invention, the particle size of metallic powder is 0.01-1000 micro meters, 0.1-800 micro meters, 0.1-600 micro meters, or greater than 0.1 micro meters.

In one embodiment of the present invention, the metallic powder particles have an elongated shape.

In one embodiment of the present invention, the gutta-percha-based material includes one paste and one powder material comprising 1-99% gutta-percha, 5-80% gutta-percha, 10-70% gutta-percha or more than 20% gutta-percha and 1-99% zinc oxide, 5-80% zinc oxide, 10-70% zinc oxide or less than 65% zinc oxide.

In one embodiment of the present invention, the gutta-percha-based material includes one paste and one powder material comprising 20% gutta-percha, 66% zinc oxide and 11% heavy metals powder.

In one embodiment of the present invention, the endodontic filling material has antibacterial properties, thus helping in infection-control after an endodontic procedure.

In one embodiment of the present invention, the endodontic filling material has X-ray radiopacity.

In one embodiment of the present invention, the endodontic filling material has mechanical properties and a melting point equivalent to, comparable to or similar to standard gutta-percha composites for endodontic applications.

The present invention further provides an endodontic point for root canal treatment, comprising: the endodontic filling material according to any one of the embodiments of the present invention, and wherein the mixture is formed into a point.

The present invention further provides a method for performing root canal treatment or the use of an electro-conductive point according to any one of the embodiments of the present invention or made of gutta-percha material combined with a metal powder in the manufacture of a medicament for root canal treatment or for use in said method, wherein the method comprises the steps of:
forming an opening in the crown;
removing the tissue in the root canal system of the tooth;
shaping the root canal;
placing the electro-conductive point into the root canal;
determining when the point is at the root canal apex with an electronic apex-locator;
stabilizing the point in place in the canal; and
filling the opening.

In one embodiment of the present invention, the method further includes the step of taking an X-ray of the tooth after the point is placed so as to view the location of the point due to its radiopacity.

In one embodiment of the present invention, the method further includes the step of adding an anti-bacterial powder component to the gutta-percha-metal powder material.

In one embodiment of the present invention, the anti-bacterial powder used is at least one selected from the group consisting of silver, titanium, iron, gold, copper, platinum, aluminum, molybdenum, zinc, tungsten, brass, carbon, nickel, palladium, tin, carbon steel, stainless steel, mercury, and their alloys, and compositions thereof.

In one embodiment of the present invention, the metal powder is a silver powder, and the composition of silver powder in the mixture is greater than 50% by weight and wherein the silver powder particles are elongated in shape and have a size greater than 0.1 micro meters.

Advantageously, utilizing this invention does not require separate or multiple tools to achieve the positioning of the gutta-percha point when an apex-locator is used as described in EP0951875 A2, which is incorporated herein by reference in its entirety.

According to the present invention the gutta-percha composite point is made electro-conductive itself, using a mixture of electro-conductive substances uniformly distributed in the matrix, and not any electro-conductive electrode (probe) or filament either embedded in the gutta-percha composite, or removable. See EP1219261 A2, WO2013181105 A1 and WO2013190539 A1, which are incorporated herein by reference in their entirety. Advantageously, this invention avoids the possible slipping of the probe outside of the point when the gutta-percha composite is softened, thus preventing a mismatching between the gutta-percha point and the electro-conductive probe which is embedded in it.

In an illustrative embodiment of the present invention an electro-conductive gutta-percha-silver composite is formed with gutta-percha exposed on the surfaces of the gutta-percha point and without any electro-conductive layer fully covering the external surfaces of the point as shown in US2008/0038697, which is incorporated herein by reference in its entirety. Advantageously, the gutta-percha remains in direct contact with the root canal system walls and provides proper sealing when melted. The application of gutta-percha is based on its capability to melt and establish mechanical adhesion to the root canal system walls, sealing the root canal system, and protecting it from bacterial colonisation. The ability to act as a good sealant is based on the fact that gutta-percha melts, precisely matching the shape of the root canal system, and establishes mechanical adhesion with the root canal system walls. If a superficial silver-plating is used, all the basic principles of endodontic sealing are lost (i.e., silver does not melt at low temperatures). It is true that the material becomes electro-conductive, but there is no gutta-percha in touch with the root canal system walls, and its efficacy as a root canal sealer is lost. The present invention does not have the problem of silver-coated gutta-percha as it is the gutta-percha itself that is in contact with the root canal system walls, as happens in traditional root canal treatment. The advantage is that, adding electro-conductive powder to the gutta-percha allows the material to have electro-conductive properties, which allow it to be directly detected by the apex-locator.

Thus the inventive step is to introduce electro-conductive properties in gutta-percha composite materials, without changing the basic principles of its clinical application. The inventive step is not related to the use of the same material, as it is well known that materials have different behaviours depending on their physical formulation. In this case silver powder is being used instead of silver plates. Silver plates been used in dentistry for decades and silver points are still used today by a very limited number of clinicians. However, the silver plates used in the prior art are rigid and cannot follow the curves usually present in the root canals. Thus the use of prior art silver plates obligates the dentist to create a straight conic-shaped cavity not well representative of the real root canal. This may limit the sealing of the root canal system because the root canal apex is not reached and there is a risk of the creation of holes in the root which are not part of the root canal system. In addition, creating the straight conic-shaped cavity may reduce the chance of removing the infected nerve tissues. The new material, which uses silver powder instead of silver plates, allows the gutta-percha composite to maintain its flexibility even though silver is used.

This invention includes an endodontic filling material, which is able to seal the root canal system following the principles of the well-established methods involving gutta-percha composites, but with additional electro-conductive properties. Advantageously, the material does not work merely as an electro-conductive probe such as that disclosed by the prior art such as JP3611843 B1, but in addition it can be directly used to seal the root canal system as well. See JP3611843 B1, which is incorporated herein by reference in its entirety.

In an exemplary embodiment, the invention uses silver powder particles, preferably >50% in weight and >0.1 µm in size, compared to other gutta-percha composites such as those disclosed in U.S. Pat. No. 4,525,147, which is incorporated herein by reference in its entirety. The % may vary. Using gutta-percha composites available on the market, and not pure gutta-percha, experiments were performed to determine the amount of gutta-percha composite material relative to the silver amount for good conductivity. The tests showed some electro-conductivity at 50% in weight, good electro-conductivity at 70% in weight, and optimum electro-conductivity at 80% in weight.

In the experiments the amount of material, relative to the silver particle size had the following effects:
Particles in the nano-meter scale are already saturated when the material is at 60% in weight.
Particles in the micro meters scale are saturated when the material is at 90% in weight. For these reasons weight >70% and size >micro meters is preferred.

However, using almost pure gutta-percha (e.g. by reducing additional radiopaque substances and zinc oxide) may allow the electro-conductivity to be obtained at lower silver % or smaller particle size. Advantageously, this invention can achieve electro-conductivity comparable with the metallic probe (file) commonly connected to an apex-locator during the standard endodontic treatment.

Mixing the gutta-percha with metallic powder can improve the thermal conductivity of the material. See U.S. Published Application US2010/0124728, which is incorporated herein by reference in its entirety. Nevertheless, improving the thermal conductivity of a material does not imply a change of its electro-conductivity. This invention has advantages in detecting the location of the tip of the gutta-percha point while still providing sealing, and also provides advantages related to enhanced thermal conductivity of the gutta-percha point. Further, the inventive material gains electro-conductivity and can be used in connection with electronic devices.

Mixing the gutta-percha with metallic powder can also improve the mechanical properties of the material. GB381774A is directed to improve the mechanical properties of a material rather than providing electro-conductivity to the gutta-percha according to the present invention, which is incorporated herein by reference in its entirety. Also, mixing gutta-percha with metallic powder can reduce the shrinkage of the material during cooling after melting. This is important to minimize the micro-leakage generated by detachment of the material from the root canal system walls during shrinkage. Nevertheless, improving the mechanical properties of a material does not imply a change of its electro-conductivity.

As mentioned above the invention consists of a gutta-percha-silver composition with the silver amount preferably >50% and particles sizes >0.1 µm, which particle size does not compromise the mechanical properties of the material. In the preferred embodiments, the particle size may be important in order to enhance the electro-conductivity without compromising the mechanical properties. If particles of very small size are used together with the increase in electro-conductivity, the gutta-percha composite may lose the biomechanical properties required for its clinical application, such as elasticity and formability. See U.S. Pat. No. 9,192,545, which is incorporated herein by reference in its entirety.

The use of gutta-percha composites for root canal treatments is the gold standard in endodontics and dentistry, and one of the most widely used practices among dentists. Advantageously, this invention allows the dentist to perform the root canal treatment following the basic principles of the treatments performed with the common gutta-percha composites, without requiring variations in the methodology undermining the efficacy of the therapy, such as recurring to thermosetting resins as described in U.S. Pat. No. 5,263,861, which is incorporated herein by reference in its entirety.

There are several advantages of the invention over currently available technology. These advantageous are as follows:

- This new composite material generates new use of the previous existing products: the endodontic points made with this new material can be used in the determination of the root canal length (they can be used with electronic devices known as apex-locators).
- This new composite material improves the use of the previous existing products: the endodontic points made with this new material can be used for the same purpose as the standard gutta-percha points, but with increased precision in the procedure (the position of the endodontic point can be determined through a very precise electronic device, the apex-locator).
- This new composite material simplifies the already existing technique: the endodontic points made with this new material can be positioned in the root canal without the need of X-rays to check the correctness of the position, because they can be connected to electronic devices (apex-locator). This can reduce the procedural time of the treatment and the number of instruments needed.
- This new composite material improves the safety of the patient: the endodontic points made with this new material can be positioned in the root canal without the need for intra-operative X-rays to check the correctness of the position, thus reducing the exposure of the patient to X-rays.
- This new composite material expands the possibilities of treatment: the endodontic points made with this new material can be positioned in the root canal without the need for X-rays to check the correctness of the position, allowing the clinicians to provide endodontic treatments even in places where there is a lack of X-ray facilities (e.g., underdeveloped countries).
- This new composite material expands the possibilities of treatment: the endodontic points made with this new material can be positioned in the root canal without the need for X-rays to check the correctness of the position, allowing the clinicians to provide safe endodontic treatments in pregnant or young growing patients, safeguarding the health of those vulnerable patients.
- This new composite material, compared to other electro-conductive endodontic materials, is the most similar to the standard non-electro-conductive gutta-percha composites, allowing the same application and standard procedures, respecting the basic principles of sealing the root canal system with gutta-percha adhering to the root canal system walls.
- The new composite material, compared to other electro-conductive endodontic materials, can have easier production procedures.
- The new composite material also has various anti-bacterial properties, contributing to the healing of the infection.
- The new composite material avoids the problem of errors generated by a mismatch between the radiographic apex and the clinical apex.

BRIEF DESCRIPTION OF THE DRAWING FIGURES

The foregoing and other objects and advantages of the present invention will become more apparent when considered in connection with the following detailed description and appended drawings in which like designations denote like elements in the various views, and wherein.

DETAILED DESCRIPTION OF EXEMPLARY EMBODIMENTS OF THE INVENTION

In the following examples, one gutta-percha composite material available from the market (20% gutta-percha, 66% zinc oxide, and 11% barium sulphate) is mixed with silver particles. Also, other components such as titanium, stainless steel, graphite and silver of different particle sizes may be used. Preferably the silver particles have an elongated shape. The formulation preferably requires a minimum of 50% silver by weight to achieve some electro-conductivity. With higher percentages of silver the electro-conductivity is improved. Also, with different gutta-percha materials (pastes), including pure gutta-percha, a smaller amount of metal powder may be needed. It is easily within the capability of one of reasonable skill in the art to try different percentages of silver or other metal powders with different gutta-percha materials to determine a minimum percentage of metal powder at which there is electro-conductivity.

While the present invention may use single metal components, it is also possible to use mixtures, e.g., mixtures of two or more of titanium, stainless steel, graphite and silver powders, as well as alloys thereof.

Particles of size <0.1 μm have worse electrical properties and, although they achieve some electro-conductivity at 50% silver by weight, they are in a saturated state compromising the mechanical properties of the material. In particular, the material may become less formable and may lose powder. On the contrary, particles >0.1 μm show some electro-conductivity at 50% silver by weight without the above-mentioned limitations. Therefore, preferably silver with particle size >10 μm and with >50% silver by weight can show conductivity comparable to the metallic probe (file) commonly mounted on the apex-locator.

Some examples showing the potential range of the present invention are as follows:

An example with a typical composition:
- Paste (20% gutta-percha, 66% zinc oxide, 11% barium sulphate) plus
- Powder (100% silver), with powder/paste ratio of 70% in weight, and
- Particle size ≈2500 micro meters, with elongated shape.

An example with less gutta-percha and less weight percentage:
- Paste (>20% gutta-percha) plus
- Powder (100% silver), with powder/paste ratio of >50% in weight, and
- Particle size >10 micro meters, with elongated shape.

As extreme example, very low gutta-percha and weight percentage:
- Paste (>1% gutta-percha) plus
- Powder (100% metal), with powder/paste ratio of >1% in weight, and
- Particle size >0.1 micro meters.

The new developed electro-conductive endodontic gutta-percha composite possesses anti-bacterial properties (e.g., against the dental microbe *Porphyromonas gingivalis*). In particular, the following materials provide both electro-conductive and anti-bacterial powder components (e.g., silver, titanium, iron, gold, copper, platinum, aluminum, molybdenum, zinc, tungsten, brass, carbon, nickel, palladium, tin, carbon steel, stainless steel, mercury, or their alloys, or compositions, or various particle sizes of different powders).

Standard root canal treatment is shown in FIG. 1. In particular, FIG. 1a shows an infected tooth with decay penetrating to the dentin that leads to pulp necrosis and an abscess at the apex of the root. In the procedure, after local anaesthesia (if required by clinical evaluation), an opening is drilled into the crown to create an access point. In FIG. 1c there is illustrated a file being used through the opening to reach the root canal system and to remove most of the nerve tissue. Next the root canal system is shaped and irrigated with antibacterial agents (such as sodium hypochlorite), which help to flush out debris and bacterial remnants as well. Then the root canal system and pulp chamber are dried.

Figure 1A:
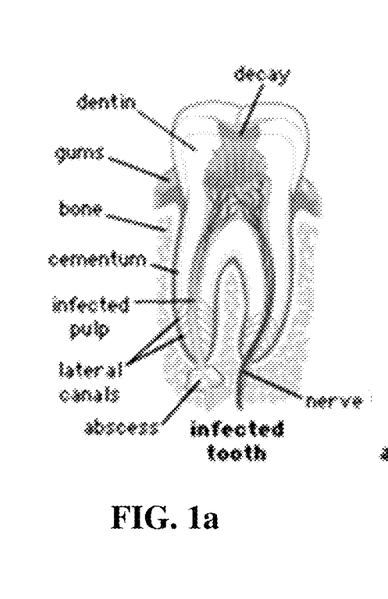
FIGS. 1a-1e illustrate a sequences of standard root canal treatment procedures.
Figure 1B:
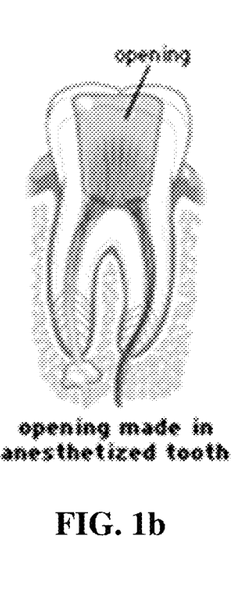
Figure 1C:
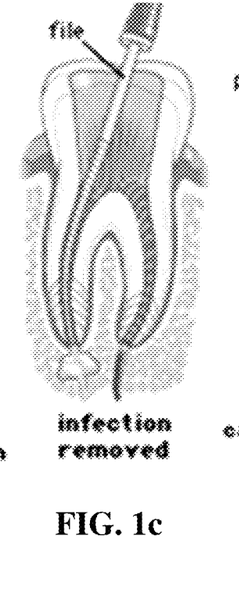
Figure 1D:
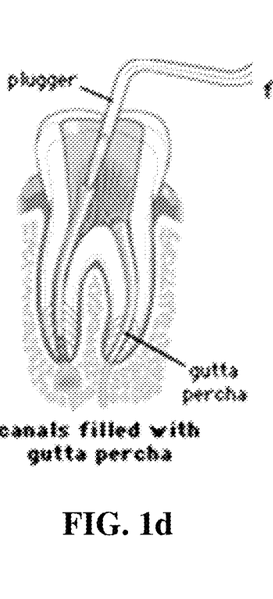

Subsequently, as shown in FIG. 1d, a plugger extends into the opening and is used to pack and fill the root canal system with heat-softened gutta-percha composite. The gutta-percha composite should be used to fill the root canal system exactly to the root canal apex. In some cases (e.g., in the lateral cold condensation technique) the gutta-percha composite is neither melted nor heat-softened, but is simply placed in the root canal and stabilized with endodontic cement. The newly developed electro-conductive gutta-percha composite is thus suitable for cold techniques as well.

Figure 1E:
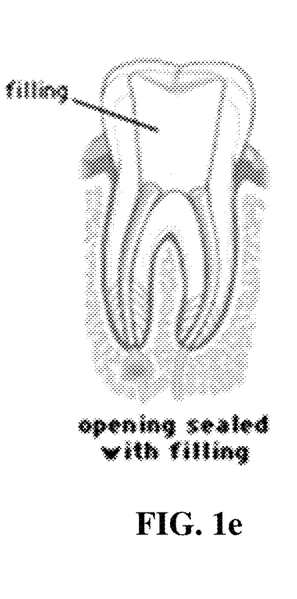

Finally in FIG. 1e the opening is sealed with a filling material. Failure to completely seal the root canal system may lead to micro-leakage and will lead to future bacterial colonization inside the root canal system, and possibly re-infection leading even to the loss of the tooth.

In order to achieve a complete filling of the root canal system to the root canal apex, it is necessary to know the length of the root canal. Measuring the length of the root canal can be achieved either by taking one or more X-rays with a metallic probe (file) of a known length inserted in the root canal and then measure it. As an alternative an apex-locator can be used to determine the location of the metallic probe (file), and then measure it. This method is the gold standard in the endodontic treatment, and the apex-locator (measuring the root canal length using electrical resistivity principles) is considered the best practice, and most dentists use this method.

The gutta-percha composite material that fills the root canal system is provided in cone-shaped points. These points have to be inserted into the tooth with their tip precisely reaching the root canal apex. Thanks to the previous length measurements, the dentist knows the length of the root canal, and can insert the gutta-percha point the right amount to reach the root canal apex. However, since a high precision is required and because the gutta-percha point may bend and the metallic probe previously used (file) is different from a gutta-percha point, after inserting the real gutta-percha point in the supposed correct position, an X-ray is necessary to check that the tip of the gutta-percha point is really at the root canal apex.

Figure 2A:
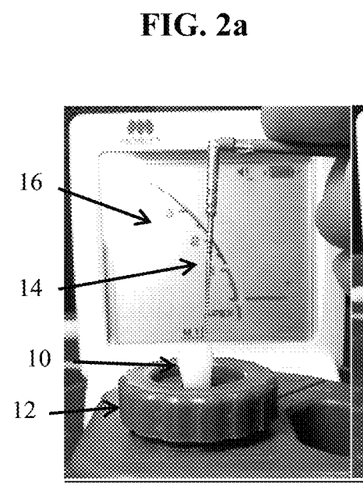
FIG. 2a illustrates positive control in which the metal probe (file) is located outside the tooth and the apex-locator shows no activity.
Figure 2B:
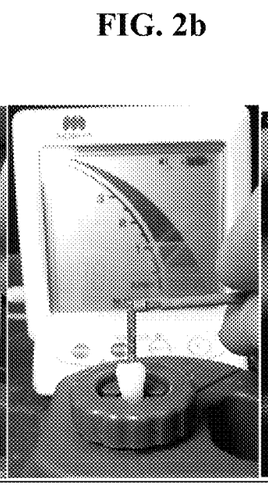
FIG. 2b illustrates the file inside the tooth with the apex-locator showing the location of the root canal apex.
Figure 2C:
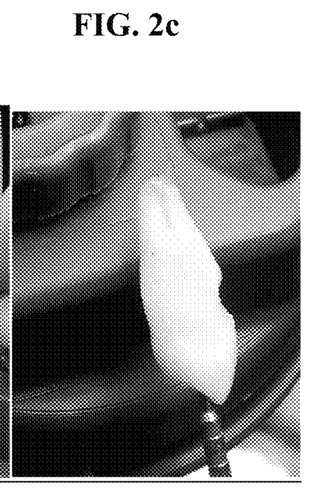
FIG. 2c illustrates a view of the tip of the file located exactly at the root canal apex.

FIG. 2a illustrates a positive control test in which the outside of the tooth 10 is surrounded by a plastic holder. The extracted tooth alone has no detectable differences in the electrical conductivity between the root canal system and the surrounding air. Therefore, to simulate the clinical situation the holder firmly stabilizes the tooth and an electro conductive gel is placed around the root. In this way, the endodontic procedures can be performed in vitro simulating the clinical environment. A metal probe or file 14 is outside the tooth and the meter 16 of the apex-locator shows no activity FIG. 2b illustrates the file inside the tooth with the apex-locator showing the location of the root canal apex on the meter. FIG. 2c illustrates a view of the tip of the file located exactly at the root canal apex.

Figure 3A:
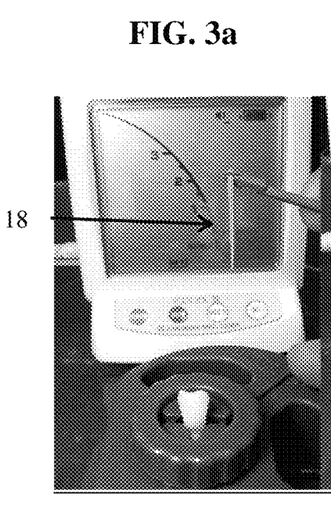
FIG. 3a illustrates negative control in which a standard gutta-percha point is located outside the tooth and the apex-locator showing no activity.
Figure 3B:
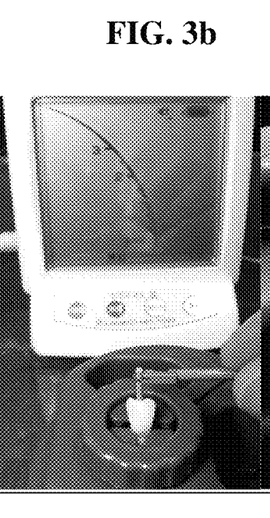
FIG. 3b illustrates the standard gutta-percha point inside the tooth and the apex-locator showing no activity.
Figure 3C:
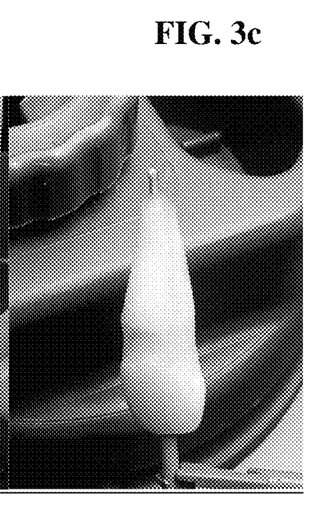
FIG. 3c illustrates a view of the tip of the standard gutta-percha point protruding out from the root canal apex.

FIG. 3a illustrates a negative control test in which a standard gutta-percha point 18 is located outside the tooth and the meter of the apex-locator shows no activity. The source of said standard gutta-percha point 18 is a manufacturer from the market, the composition is 20% gutta-percha, 66% ZnO, 11% BaSO$_4$, 3% wax. In FIG. 3b the standard gutta-percha point is inside the tooth and the apex-locator still shows no activity because it has no electro-conductive properties. FIG. 3c shows the tip of the standard gutta-percha point protruding out from the root canal apex.

Figure 4A:
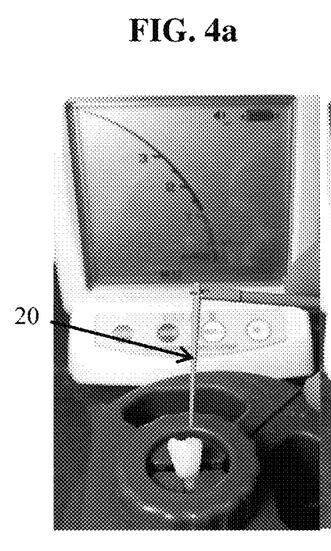
FIG. 4a illustrates a test of the electro-conductive gutta-percha point located outside the tooth and the apex-locator showing no activity.
Figure 4B:
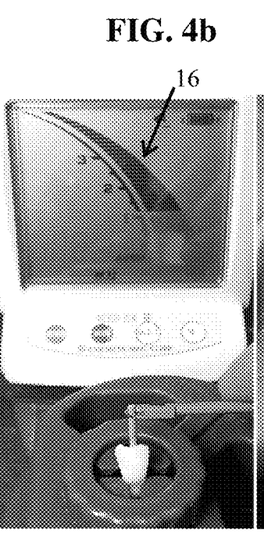
FIG. 4b illustrates the electro-conductive gutta-percha point inside the tooth with apex-locator showing its location at the root canal apex.
Figure 4C:
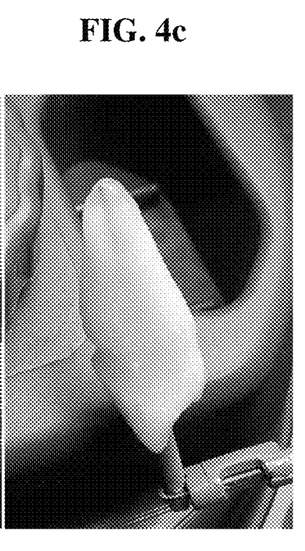
FIG. 4c shows a view of the tip of the electro-conductive gutta-percha point located exactly at the root canal apex.

FIG. 4 illustrates a test of the electro-conductive gutta-percha point of the present invention. The composition of said electro-conductive gutta-percha point is 70% Ag, 6% gutta-percha, 20% ZnO, 3% BaSO$_4$, 1% wax, which is prepared by the process illustrated in the FIG. 5. FIG. 4a shows the point 20 according to the present invention located outside the tooth and the apex-locator showing no activity. In FIG. 4b the electro-conductive gutta-percha point is shown inside the tooth with apex-locator meter 16 showing its location at the root canal apex. FIG. 4c shows the tip of the electro-conductive gutta-percha point located exactly at the root canal apex.

Figure 5A:
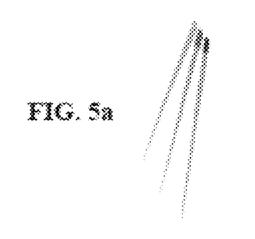
FIGS. 5a-g illustrate an example of the process for preparing the electro-conductive gutta-percha point illustrated in the FIG. 4 of the present invention.
Figure 5B:
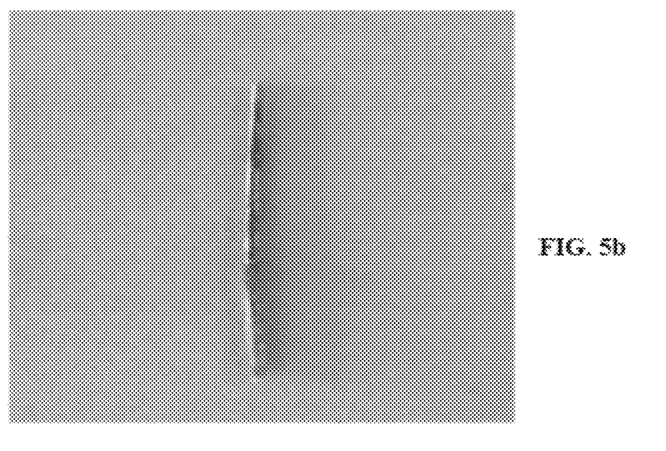
Figure 5C:
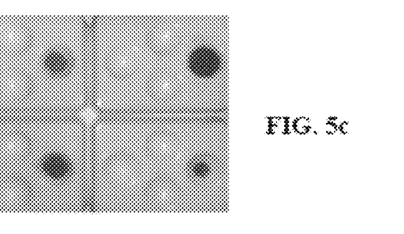
Figure 5D:
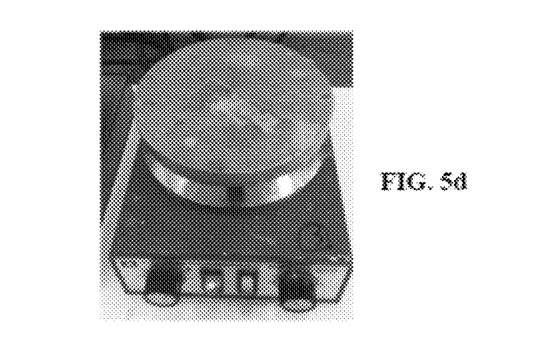
Figure 5E:
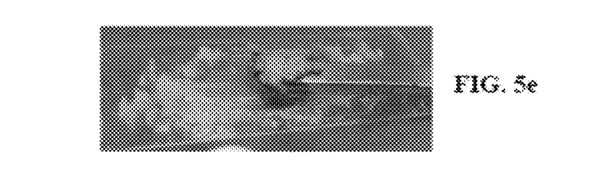
Figure 5F:
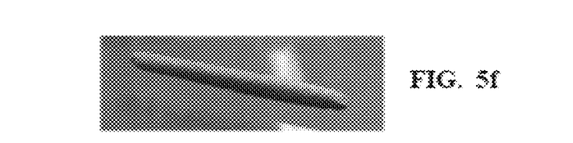
Figure 5G:
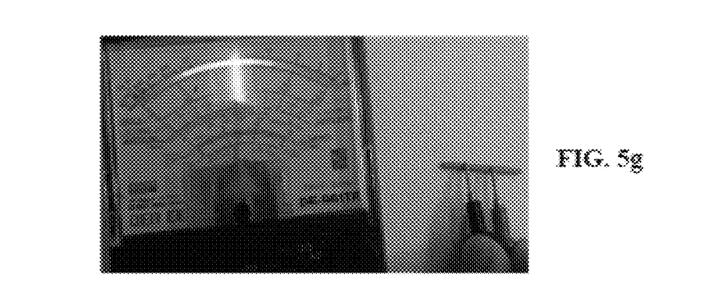
Figure 6A:
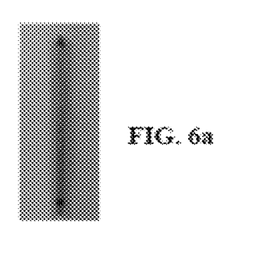
FIGS. 6a-i show the pictures of the filler material used in the examples of the present description.
Figure 6B:
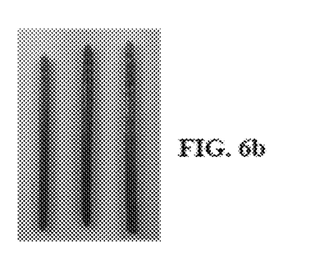
Figure 6C:
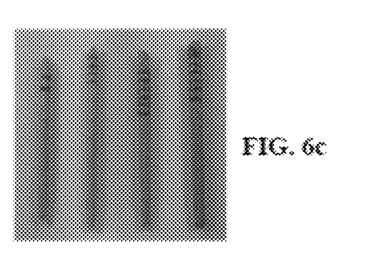
Figure 6D:
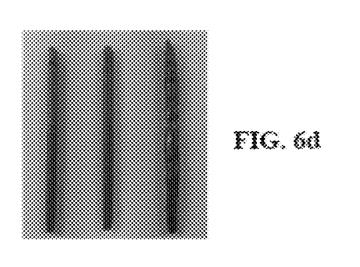
Figure 6E:
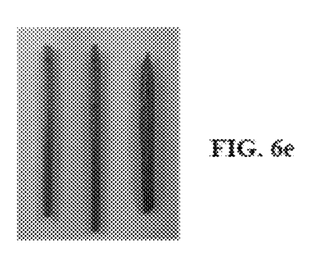
Figure 6F:
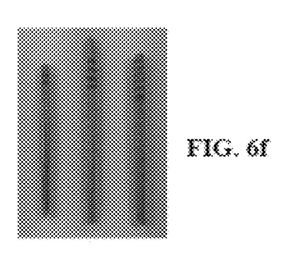
Figure 6G:
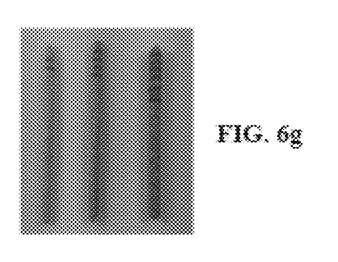
Figure 6H:
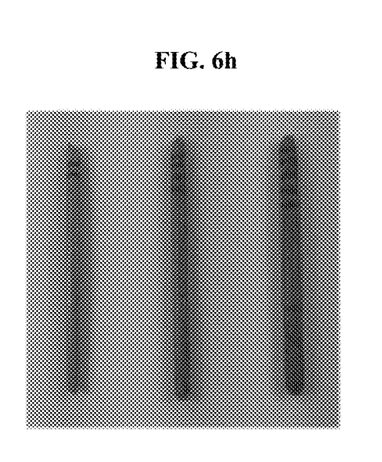
Figure 6I:
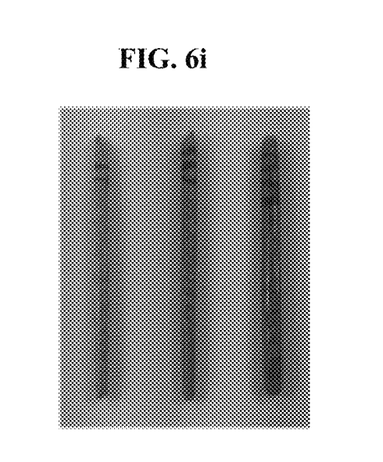

FIGS. 5a-g illustrate an example of the process for preparing the electro-conductive gutta-percha point illustrated in the FIG. 4 of the present invention, which comprises the following steps:

a) Providing gutta-percha composite from the market, c.f. FIG. 5a.
b) Providing the metal from the market, c.f. FIG. 5b.
c) Preparing a metal powder from by milling the metal, c.f. FIG. 5c.
d) Softening the gutta-percha composite on a heating plate, c.f. FIG. 5d.
e) Adding the necessary amount of metal powder to the softened gutta-percha composite and mixing the two components with a spatula to form a composite material, c.f. FIG. 5e.

f) Rolling the new composite material to give the desired shape, c.f. FIG. 5f.

g) Verifying the electro-conductivity of the material, c.f. FIG. 5g.

The same preparing process is used to prepare electro-conductive gutta-percha points with filler material selected from titanium (Ti), stainless steel (SS), graphite (C), and silver (Ag) powders having small (S) and big (B) particle size and different filing percentage (10% to 90%). Moreover, the resistivity and the mechanical properties are tested for the above electro-conductive gutta-percha points.

The electrical resistivity is measured by a known instrument (multimeter/ohmmeter) by contacting two metallic probes (input terminals) of the instrument with the electro-conductive gutta-percha points with a distance (expressed in mm) between the tips of said two metallic probes.

The parameters for the preparation of said electro-conductive gutta-percha points and their test results are shown in the following tables.

TABLE 1a

RESISTIVITY (ohm)

FILLER ($g/g_{tot}$)

| Matrix Material | Particle Material | Particle size | 10% Distance (mm) | | | | | 20% Distance (mm) | | | | |
|---|---|---|---|---|---|---|---|---|---|---|---|---|
| | | | 1 | 5 | 10 | 20 | 30 | 1 | 5 | 10 | 20 | 30 |
| Gutta percha (21%), ZnO (66%), BaSO$_4$(11%), wax (3%) | Ti | S | I | I | I | I | I | I | I | I | I | I |
| | | B | I | I | I | I | I | I | I | I | I | I |
| | SS | S | I | I | I | I | I | I | I | I | I | I |
| | | B | I | I | I | I | I | I | I | I | I | I |
| | C | S | I | I | I | I | I | I | I | I | I | I |
| | | B | I | I | I | I | I | $2*10^4$ | $3*10^4$ | $5*10^4$ | $1*10^5$ | $1*10^5$ |
| | Ag | S | I | I | I | I | I | I | I | I | I | I |
| | | M | I | I | I | I | I | I | I | I | I | I |
| | | B | I | I | I | I | I | I | I | I | I | I |

TABLE 1b

RESISTIVITY (ohm)

FILLER ($g/g_{tot}$)

| matrix Material | Particle Material | Particle size | 30% Distance (mm) | | | | | 40% Distance (mm) | | | | |
|---|---|---|---|---|---|---|---|---|---|---|---|---|
| | | | 1 | 5 | 10 | 20 | 30 | 1 | 5 | 10 | 20 | 30 |
| Gutta percha (21%), ZnO (66%), BaSO$_4$(11%), wax (3%) | Ti | S | I | I | I | I | I | 10 | 20 | 20 | 50 | 50 |
| | | B | $1*10^2$ | $2*10^2$ | $3*10^2$ | $5*10^2$ | $2*10^3$ | 8 | 16 | 25 | 40 | $2*10^2$ |
| | SS | S | I | I | I | I | I | I | I | I | I | I |
| | | B | I | I | I | I | I | I | I | I | I | I |
| | C | S | $8*10^3$ | $1*10^4$ | $2*10^4$ | $2*10^4$ | $3*10^4$ | R | R | R | R | R |
| | | B | $5*10^2$ | $8*10^2$ | $8*10^2$ | $8*10^2$ | $1*10^3$ | R | R | R | R | R |
| | Ag | S | I | I | I | I | I | I | I | I | I | I |
| | | M | I | I | I | I | I | I | I | I | I | I |
| | | B | I | I | I | I | I | I | I | I | I | I |

TABLE 1c

RESISTIVITY (ohm)

FILLER ($g/g_{tot}$)

| matrix Material | Material | Particle size | 50% Distance (mm) | | | | | 60% Distance (mm) | | | | |
|---|---|---|---|---|---|---|---|---|---|---|---|---|
| | | | 1 | 5 | 10 | 20 | 30 | 1 | 5 | 10 | 20 | 30 |
| Gutta percha (21%), ZnO (66%), BaSO$_4$ (11%), wax (3%) | Ti | S | 8 | 8 | 10 | 12 | 15 | R | R | R | R | R |
| | | B | R | R | R | R | R | R | R | R | R | R |
| | SS | S | I | I | I | I | I | $10*10^3$ | $10*10^3$ | $15*10^3$ | $20*10^3$ | $30*10^3$ |
| | | B | $2*10^3$ | $5*10^3$ | $10*10^3$ | $20*10^3$ | I | 60 | $3*10^2$ | $4*10^2$ | $7*10^2$ | $2*10^3$ |
| | C | S | R | R | R | R | R | R | R | R | R | R |
| | | B | R | R | R | R | R | R | R | R | R | R |
| | Ag | S | I | I | I | I | I | R | R | R | R | R |
| | | M | I | I | I | I | I | 50 | $10*10^2$ | $10*10^3$ | I | I |
| | | B | I | I | I | I | I | 50 | $10*10^2$ | $10*10^3$ | I | I |

TABLE 1d

| | | | RESISTIVITY (ohm) | | | | | | | | | | | | | | |
|---|---|---|---|---|---|---|---|---|---|---|---|---|---|---|---|---|---|
| | | | FILLER (g/g$_{tot}$) | | | | | | | | | | | | | | |
| matrix | | Particle | 70% Distance (mm) | | | | | 80% Distance (mm) | | | | | 90% Distance (mm) | | | | |
| Material | Material | size | 1 | 5 | 10 | 20 | 30 | 1 | 5 | 10 | 20 | 30 | 1 | 5 | 10 | 20 | 30 |
| Gutta percha | Ti | S | R | R | R | R | R | R | R | R | R | R | R | R | R | R | R |
| (21%), ZnO | | B | R | R | R | R | R | R | R | R | R | R | R | R | R | R | R |
| (66%), | SS | S | 5 * 10$^3$ | 10 * 10$^3$ | 15 * 10$^3$ | 20 * 10$^3$ | 30 * 10$^3$ | R | R | R | R | R | R | R | R | R | R |
| BaSO$_4$ | | B | R | R | R | R | R | R | R | R | R | R | R | R | R | R | R |
| (11%), | C | S | R | R | R | R | R | R | R | R | R | R | R | R | R | R | R |
| wax (3%) | | B | R | R | R | R | R | R | R | R | R | R | R | R | R | R | R |
| | Ag | S | R | R | R | R | R | R | R | R | R | R | R | R | R | R | R |
| | | M | 5 | 5 | 5 | 5 | 5 | 5 | 5 | 5 | 5 | 5 | R | R | R | R | R |
| | | B | 5 | 5 | 5 | 5 | 5 | 5 | 5 | 5 | 5 | 5 | R | R | R | R | R |

Note:

I = infinite (means that resistivity is almost infinite, while very small conductivity may be present but might not be detectable with the ohmmeter.)

R = saturated (means that with the technique used during the experiment to mix the metallic powder with the guttapercha composite, at that point a limit is reached and no more powder can be added in the mixture, i.e. the composite material is saturated (full). Depending on the material and on the particle size, different percentages of powder are necessary to reach saturation of the mixture. Probably with different mixing techniques/temperatures the saturation percentage can change.)

TABLE 2a

| | | | Quality of the mechanical properties | | | | | | | | | |
|---|---|---|---|---|---|---|---|---|---|---|---|---|
| | | | FILLER (g/g$_{tot}$) | | | | | | | | | |
| Matrix | | Particle | 10% Distance (mm) | | | | | 20% Distance (mm) | | | | |
| Material | Material | size | 1 | 5 | 10 | 20 | 30 | 1 | 5 | 10 | 20 | 30 |
| Gutta percha (21%), ZnO (66%), | Ti | S | G | G | G | G | G | G | G | G | G | G |
| BaSO$_4$ (11%), wax (3%) | | B | G | G | G | G | G | G | G | G | G | G |
| | SS | S | G | G | G | G | G | G | G | G | G | G |
| | | B | G | G | G | G | G | G | G | G | G | G |
| | C | S | G | G | G | G | G | G | G | G | G | G |
| | | B | G | G | G | G | G | G | G | G | G | G |
| | Ag | S | G | G | G | G | G | G | G | G | G | G |
| | | M | G | G | G | G | G | G | G | G | G | G |
| | | B | G | G | G | G | G | G | G | G | G | G |

TABLE 2b

| | | | Quality of the mechanical properties | | | | | | | | | |
|---|---|---|---|---|---|---|---|---|---|---|---|---|
| | | | FILLER (g/g$_{tot}$) | | | | | | | | | |
| Matrix | | Particle | 30% Distance (mm) | | | | | 40% Distance (mm) | | | | |
| Material | Material | size | 1 | 5 | 10 | 20 | 30 | 1 | 5 | 10 | 20 | 30 |
| Gutta percha (21%), ZnO (66%), | Ti | S | G | G | G | G | G | A | A | A | A | A |
| BaSO$_4$ (11%), wax (3%) | | B | G | G | G | G | G | P | P | P | P | P |
| | SS | S | G | G | G | G | G | G | G | G | G | G |
| | | B | G | G | G | G | G | G | G | G | G | G |
| | C | S | P | P | P | P | P | | | | | |
| | | B | P | P | P | P | P | | | | | |
| | Ag | S | G | G | G | G | G | G | G | G | G | G |
| | | M | G | G | G | G | G | G | G | G | G | G |
| | | B | G | G | G | G | G | G | G | G | G | G |

TABLE 2c

Quality of the mechanical properties

| matrix Material | Particle Material | size | FILLER (g/g_tot) 50% Distance (mm) | | | | | 60% Distance (mm) | | | | |
|---|---|---|---|---|---|---|---|---|---|---|---|---|
| | | | 1 | 5 | 10 | 20 | 30 | 1 | 5 | 10 | 20 | 30 |
| Gutta percha (21%), ZnO (66%), BaSO$_4$ (11%), wax (3%) | Ti | S | P | P | P | P | P | | | | | |
| | | B | | | | | | | | | | |
| | SS | S | G | G | G | G | G | A | A | A | A | A |
| | | B | A | A | A | A | A | P | P | P | P | P |
| | C | S | | | | | | | | | | |
| | | B | | | | | | | | | | |
| | Ag | S | P | P | P | P | P | | | | | |
| | | M | G | G | G | G | G | G | G | G | G | G |
| | | B | G | G | G | G | G | G | G | G | G | G |

TABLE 2d

Quality of the mechanical properties

| matrix Material | Particle Material | size | FILLER (g/g_tot) 70% Distance (mm) | | | | | 80% Distance (mm) | | | | | 90% Distance (mm) | | | | |
|---|---|---|---|---|---|---|---|---|---|---|---|---|---|---|---|---|---|
| | | | 1 | 5 | 10 | 20 | 30 | 1 | 5 | 10 | 20 | 30 | 1 | 5 | 10 | 20 | 30 |
| Gutta percha (21%), ZnO (66%), BaSO$_4$ (11%), wax (3%) | Ti | S | | | | | | | | | | | | | | | |
| | | B | | | | | | | | | | | | | | | |
| | SS | S | P | P | P | P | P | | | | | | | | | | |
| | | B | | | | | | | | | | | | | | | |
| | C | S | | | | | | | | | | | | | | | |
| | | B | | | | | | | | | | | | | | | |
| | Ag | S | | | | | | | | | | | | | | | |
| | | M | A | A | A | A | A | P | P | P | P | P | | | | | |
| | | B | G | G | G | G | G | P | P | P | P | P | | | | | |

Note:
P = poor
A = acceptable
G = good
distance (mm) = the distance, expressed in mm, between the tips of the two metallic probes (input terminals) of the instrument to measure the electrical resistivity (multimeter/ohmmeter)

While the present invention has been particularly shown and described with reference to preferred embodiments thereof; it will be understood by those skilled in the art that various changes in form and details may be made therein without departing from the spirit and scope of the invention.

The invention claimed is:

1. An endodontic filling material for root canal treatment, comprising:
a gutta-percha-based material; and
a metallic powder having particles greater than 10 μm, wherein at least 70% by weight of the metallic powder is mixed with the gutta-percha-based material so as to form a mixture exhibiting electro-conductivity that is detectable with an electronic apex-locator.

2. The endodontic filling material of claim 1, wherein the metallic powder is a powder of at least one of silver, titanium, stainless steel, graphite, aluminium, copper, and gold, or mixtures thereof.

3. The endodontic filling material of claim 2, wherein the metallic powder is a silver powder.

4. The endodontic filling material of claim 1, wherein the amount of the metallic powder in the mixture is 70-80% by weight.

5. The endodontic filling material of claim 1, wherein the metallic powder particles have an elongated shape.

6. The endodontic filling material of claim 1, wherein the gutta-percha-based material includes one paste and one powder material comprising more than 20% gutta-percha.

7. An endodontic filling material for root canal treatment comprising:
a gutta-percha-based material; and
a metallic powder, wherein the metallic powder is mixed with the gutta-percha-based material in sufficient quantity to form a mixture exhibiting electro-conductivity that is detectable with an electronic apex-locator, and wherein the gutta-percha-based material includes one paste and one powder material comprising 20% gutta-percha, 66% zinc oxide and 11% heavy metals powder.

8. The endodontic filling material of claim 1, wherein the gutta-percha-based material includes an anti-bacterial powder component.

9. The endodontic filling material of claim 8, wherein the anti-bacterial powder is selected from the group consisting of silver, titanium, iron, gold, copper, platinum, aluminum, molybdenum, zinc, tungsten, brass, carbon, nickel, palladium, tin, carbon steel, stainless steel, mercury, and their alloys, and mixtures thereof.

10. The endodontic filling material of claim 1, wherein the endodontic filling material has antibacterial properties and assists in infection control after an endodontic procedure.

11. The endodontic filling material of claim 1, wherein the endodontic filling material has X-ray radiopacity.

12. An endodontic point for root canal treatment, comprising:
the endodontic filling material of claim 1, wherein the mixture formed from the gutta-percha-based material and the metallic powder is formed into a point.

13. A method for performing root canal treatment, the method comprising the steps of:
forming an opening in a crown of a tooth;
removing tissue in a root canal system of the tooth;
shaping the root canal;
placing the endodontic point of claim 12 into the root canal;
determining when the endodontic point is at the root canal apex with an electronic apex-locator;
stabilizing the endodontic point in place in the root canal; and
filling the opening.

14. The method of claim 13, wherein the method further includes the step of taking an X-ray of the tooth after the point is placed in the root canal so as to view the location of the point due to its radiopacity.

15. The method of claim 13, wherein the method further includes the step of adding an anti-bacterial powder component to the gutta-percha-metal powder material of the endodontic point.

16. The method of claim 15, wherein the anti-bacterial powder is selected from the group consisting of silver, titanium, iron, gold, copper, platinum, aluminum, molybdenum, zinc, tungsten, brass, carbon, nickel, palladium, tin, carbon steel, stainless steel, mercury, and their alloys, and mixtures thereof.

17. The method of claim 13, wherein the metallic powder of the endodontic point is a silver powder, and the composition of silver powder in the mixture of the endodontic filling material is greater than 50% by weight.

18. The method of claim 17, wherein the silver powder is comprised of particles that are elongated in shape and have a size greater than 0.1 micrometers.

* * * * *